United States Patent [19]
Christopherson et al.

[11] Patent Number: 5,908,743
[45] Date of Patent: Jun. 1, 1999

[54] GAG GENE PRIMERS FOR THE DETECTION OF HIV-1

[75] Inventors: Cindy Dawn Christopherson, San Francisco; Shirley Yee Kwok, San Ramon; Shi-Da Yu Lu, Cupertino, all of Calif.

[73] Assignee: Roche Molecular Systems, Inc., Pleasanton, Calif.

[21] Appl. No.: 09/004,949

[22] Filed: Jan. 9, 1998

Related U.S. Application Data

[60] Provisional application No. 60/037,744, Jan. 17, 1997.
[51] Int. Cl.$^6$ .............................. C12Q 1/68; C07H 21/04; C12P 19/34
[52] U.S. Cl. ................................. 435/5; 435/6; 435/91.2; 435/810; 536/24.32; 536/24.33
[58] Field of Search .................................. 435/6, 91.2, 5, 435/810; 536/24.32, 24.33

[56] References Cited

U.S. PATENT DOCUMENTS

| | | | |
|---|---|---|---|
| 5,386,022 | 1/1995 | Sninsky et al. | 536/24.32 |
| 5,389,512 | 2/1995 | Sninsky et al. | 435/5 |
| 5,599,662 | 2/1997 | Respess | 435/5 |
| 5,695,926 | 12/1997 | Cros et al. | 435/5 |
| 5,702,926 | 12/1997 | Cummins et al. | 435/6 |

FOREIGN PATENT DOCUMENTS

617132 A2   9/1994   European Pat. Off. .

OTHER PUBLICATIONS

Kwok et al., 1990, "Effects of Primer—Template Mismatches on the Polymerase Chain Reaction: Human Immunodeficiency Virus Type 1 Model Studies," *Nucleic Acids Research*, 18 (4): 999–1005.

Kellogg et al., 1990, "Detection of Human Immunodeficiency Virus," *PCR Protocols: A Guide to Methods and Applications*: 337–347.

Jackson et al., 1991, "Non–isotopic Polymerase Chain Reaction Methods for the Detection of HIV–1 in Ugandan Mothers and Infants," *AIDS* 5 1463–1467.

Coutlée et al., 1991, "The Polymerase Chain Reaction: A New Tool for the Understanding and Diagnosis of HIV–1 Infection at the Molecular Level," *Molecular and Cellular Probes* 5:241–259.

1993 Product Insert for Amplicor™ HIV–1 Test, pp. 1–11.

Kwok et al., 1994, "A Guide to the Design and Used of Mismatched and Degenerate Primers," *PCR Methods & Applications* 3:S39–S47.

Fransen et al., 1994, "Design and Evaluation of New, Highly Sensitive and Specific Primers for Polymerase Chain Reaction Detection of HIV–1 Infected Primary Lymphocytes," *Molecular and Cellular Probes* 8: 317–322.

Meyers et al., 1994 Human Retroviruses and AIDS, Los Alamos National Laboratory, Los Alamos New Mexico: pp. I1–IA49.

Arnold et al., Nov. 1995, "HIV Type 1 Sequence Subtype G Transmission From Mother to Infant: Failure of Variant Sequence Species to Amplify in the Roche Amplicor Test," *AIDS Research and Human Retroviruses* 11(8): 999–1001.

Meyers et al., 1996 Human Retroviruses and AIDS, Los Alamos National Laboratory, Los Alamos New Mexico: pp. I1–I19 and I93–I128.

1996 Product Insert for Amplicor HIV–1 Monitor™ Test, pp. 1–30.

Lyamuya et al., Jan. 1997, "Comparison of In–House and Commercial Sample Preparation and PCR Amplification Systems for Detection of Human Immunodeficiency Virus type 1 DNA in Blood Samples from Tanzanian Adults," *Journal of Clinical Microbiology* 35 (1): 278–280.

*Primary Examiner*—Carla J. Myers
*Attorney, Agent, or Firm*—Douglas A. Petry

[57] ABSTRACT

The present invention provides improved primers for the polymerase chain reaction (PCR) amplification of a nucleic acid sequence from the gag gene of the human immunodeficiency virus type 1 (HIV-1). The primers and amplification methods of the invention enable the detection of all HIV-1 group M isolates with nearly uniform efficiency.

15 Claims, No Drawings

```
                         SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:1:

AGTGGGGGGA CATCAAGCAG CCATGCAAAT                                             30

(2) INFORMATION FOR SEQ ID NO:2:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:2:

AGTGGGGGGA CACCAGGCAG CAATGCAAAT                                             30

(2) INFORMATION FOR SEQ ID NO:3:

(i) SEQUENCE CHARACTERISTICS:
           (A) LENGTH: 28 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:3:

TACTAGTAGT TCCTGCTATG TCACTTCC                                               28

(2) INFORMATION FOR SEQ ID NO:4:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:4:

TGAAGGGTAC TAGTAGTTCC TGCTAT                                                 26
```

-continued (2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

AGTTGGAGGA CATCAAGCAG CCATGCAAAT      30

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TGCTATGTCA GTTCCCCTTG GTTCTCT      27

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TGCTATGTCA CTTCCCCTTG GTTCTCT      27

GAG GENE PRIMERS FOR THE DETECTION OF HIV-1

This application claims priority to U.S. Provisional application Ser. No. 60/037744, filed Jan. 17, 1997, which is incorporated herein by reference.

BACKGROUND OF THE INVENTION

1. Field of the Invention

The present invention relates to the field of molecular biology and nucleic acid chemistry. More specifically, it relates to methods and reagents for detecting human immunodeficiency virus type 1 (HIV-1). The invention therefore has applications in the field of medicine generally, medical diagnostics specifically, and the field of molecular biology.

2. Description of Related Art

The invention of methods for amplifying specific sequences of nucleic acids, in particular, the polymerase chain reaction (PCR), makes possible the rapid detection of nucleic acids present in a sample in what was previously an undetectably low quantity (see U.S. Pat. Nos. 4,683,195; 4,683,202; and 4,965,188, each of which is incorporated herein by reference). The development and application of PCR are described extensively in the literature. For example, a range of PCR-related topics are discussed in PCR Technology—principles and applications for DNA amplification, 1989, (ed. H. A. Erlich) Stockton Press, New York, N.Y.; PCR Protocols: A guide to methods and applications, 1990, (ed. M. A. Innis et al.) Academic Press, San Diego, Calif.; and PCR Strategies, 1995, (ed. M. A. Innis et al.) Academic Press, San Diego, Calif.; each of which is incorporated herein by reference. Commercial vendors, such as Perkin Elmer (Norwalk, Conn.), market PCR reagents and publish PCR protocols.

The use of PCR and probe hybridization to amplify and detect HIV-1 nucleic acid is reviewed in Kwok, 1992, *Ann. Med.* 24:211–214; and Coutlee et al., 1991, *Mol. Cel. Probes* 5:241–259; both incorporated herein by reference. PCR-based HIV-1 detection assays are described in, for example, U.S. Pat. Nos. 5,008,182 and 5,176,775; Kellogg and Kwok, 1990, in PCR Protocols: A Guide to Methods and Applications, (ed. Innis et al.), Academic Press, San Diego, Calif.:337–347; Holodniy et al., 1991, *J. Inf. Dis.* 163:802–865; Jackson et al., 1991, *AIDS* 5:1463–1467; and Mulder et al, 1994, *J. Clin. Microbiol.* 32(2):292–300; each incorporated herein by reference.

Commercial kits for the amplification and detection of HIV-1 are commercially available from Hoffmann-La Roche (Nutley, N.J.). The Amplicor™ HIV-1 Test is an in vitro assay for the detection of HIV-1 proviral DNA. The AMPLICOR HIV-1 MONITORTM™ Test is an in vitro assay for the quantitation of HIV-1 RNA. The Amplicor HIV-1 Test product insert and the AMPLICOR HIV-1 MONITOR Test product insert are each incorporated herein by reference. Both of the Amplicor assays amplify HIV-1 nucleic acids using the primer pair SK462 (SEQ ID NO: 5) and SK431 (SEQ ID NO: 6), described in Mulder et al., 1994, *J. Clin. Microbiol.* 32(2):292–300, and referred to herein as the Amplicor HIV-1 primers.

HIV-1 displays considerable genomic sequence variability. Phylogenetic analysis of the nucleic acid sequences of HIV-1 gag and env genes is described in Myers et al, 1993, Human Retrovirus and AIDS 1993, Los Alamos National Laboratory, Los Alamos, N.Mex., incorporated herein by reference. Within the M group, subtypes A–J have been identified.

Conventional techniques of molecular biology and nucleic acid chemistry, which are within the skill of the art, are fully explained fully in the literature. See, for example, Sambrook et al., 1989, *Molecular Cloning—A Laboratory Manual,* Cold Spring Harbor Laboratory, Cold Spring Harbor, N.Y.; *Oligonucleotide Synthesis* (M. J. Gait, ed., 1984); *Nucleic Acid Hybridization* (B. D. Hames and S. J. Higgins. eds., 1984); and a series, *Methods in Enzymology* (Academic Press, Inc.), all of which are incorporated herein by reference. All patents, patent applications, and publications cited herein, both supra and infra, are incorporated herein by reference.

SUMMARY OF THE INVENTION

We have identified a number of human immuno deficiency virus type 1 (HIV-1) group M isolates which either are not amplifiable or not amplifiable efficiently using previously described gag gene primers, in particular, the Amplicor HIV-1 primers, SK462 (SEQ ID NO: 5) and SK431 (SEQ ID NO: 6). These isolates exhibit previously unseen sequence variability within the region encompassing the primer binding sites of the Amplicor HIV-1 primers. The present invention provides improved primers which enable efficient amplification from these newly discovered isolates, in addition to all isolates amplifiable with the Amplicor HIV-1 primers. Moreover, the primers of the present invention enable amplification from all known HIV-1 group M isolates with nearly uniform efficiency.

One aspect of the present invention relates to improved oligonucleotide primers which enable the polymerase chain reaction (PCR) amplification of a region of the gag gene from HIV-1 group M isolates from subtypes A–G with nearly uniform efficiency and without the simultaneous amplification of non-target sequences.

Another aspect of the invention relates to improved methods for amplifying a region of the gag gene from HIV-1 group M subtypes which comprise carrying out a PCR using the primers of the invention.

Another aspect of the invention relates to kits which contain an amplification primer of the present invention. These kits can include additional reagents, such as the detection probes or one or more amplification reagents, e.g., polymerase, buffers, and nucleoside triphosphates.

DETAILED DESCRIPTION OF THE INVENTION

To aid in understanding the invention, several terms are defined below.

The terms "nucleic acid" and "oligonucleotide" refer to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA.

Oligonucleotides can be prepared by any suitable method, including, for example, cloning and restriction of appropriate sequences and direct chemical synthesis by a method such as the phosphotriester method of Narang et al., 1979, *Meth. Enzymol.* 68:90–99; the phosphodiester method of Brown et al, 1979, *Meth. Enzyol.* 68:109–151; the diethylphosphoramidite method of Beaucage et al, 1981, *Tetrahedron Lett.* 22:1859–1862; and the solid support method of U.S. Pat. No. 4,458,066, each incorporated herein by reference. A review of synthesis methods is provided in Goodchild, 1990, *Bioconjugate Chemistry* 1(3):165–187, incorporated herein by reference.

The term "hybridization" refers the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which only fully complementary nucleic acid strands will hybridize are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair concentration of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, N.Y.; and Wetmur, 1991, *Critical Reviews in Biochem. and Mo. Biol.* 26(3/4):227–259; both incorporated herein by reference).

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from 15 to 35 nucleotides. Short primer molecules generally require cooler temperatures to form sufficiently stable hybrid complexes with the template. A primer need not reflect the exact sequence of the template nucleic acid, but must be sufficiently complementary to hybridize with the template. Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning of the amplified product. The region of the primer which is sufficiently complementary to the template to hybridize is referred to herein as the hybridizing region.

As used herein, the "upstream" primer refers to the primer whose extension product is a subsequence of the coding strand. The "downstream" primer refers to the primer whose extension product is a subsequence of the complementary non-coding strand.

The terms "target sequence", "target region", and "target nucleic acid" refer to a region of a nucleic acid which is to be amplified, detected, or otherwise analyzed.

As used herein, a primer is "specific" for a target sequence if the number of mismatches present between the primer and the target sequence is less than the number of mismatches present between the primer and non-target sequences which might be present in a sample. Hybridization conditions can be chosen under which stable duplexes are formed only if the number of mismatches present is no more than the number of mismatches present between the primer and the target sequence. Under such conditions, the target-specific primer can form a stable duplex only with a target sequence. Thus, the use of target-specific primers under suitably stringent amplification conditions enables the specific amplification of those sequences which contain the target primer binding sites. Similarly, the use of target-specific probes under suitably stringent hybridization conditions enables the detection of a specific target sequence.

The term "amplification reaction mixture" refers to a solution containing reagents necessary to carry out an amplification reaction, and typically contains primers, a thermostable DNA polymerase, dNTP's, and a divalent metal cation in a suitable buffer. A reaction mixture is referred to as complete if it contains all reagents necessary to carry out the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction components which includes primers of the present invention.

HIV-1 Amplification Primers

The present primers enable amplification of nucleic acid from the HIV-1 group M subtypes. The primers represent a significant improvement over primers previously described in that they enable amplification of nucleic acid from a region of the gag gene from all isolates of subtypes A–G belonging to Group M with nearly uniform efficiency, including the newly discovered isolates. The nucleotide sequences of the primers are provided below, shown left to right in a 5' to 3' orientation.

| Upstream Primers | |
|---|---|
| SK145 (SEQ ID NO: 1) | AGTGGGGGGACATCAAGCAGCCATGCAAAT |
| SK145M2 (SEQ ID NO: 2) | AGTGGGGGGACACCAGGCAGCAATGCAAAT |
| Downstream Primers | |
| SKCCI (SEQ ID NO: 3) | TACTAGTAGTTCCTGCTATGTCACTTCC |
| SKCC3 (SEQ ID NO: 4) | TGAAGGGTACTAGTAGTTCCTGCTAT |

The downstream primers of the present invention may be used with any of the upstream primers disclosed herein. The downstream primers of the present invention are preferably used with upstream primer SK145 (SEQ ID NO: 1), optionally in conjunction with upstream primer SK145M2 (SEQ ID NO: 2). Upstream primer SK145 (SEQ ID NO: 1) is described in Kellogg and Kwok, 1990, in PCR Protocols: A Guide to Methods and Applications, (ed. Innis et al.), Academic Press, San Diego, Calif.:337–347. The second upstream primer, SK145M2 (SEQ ID NO: 2), hybridizes in the same region as SK145 (SEQ ID NO: 1), but is designed to more closely match the nucleotide sequence of certain HIV-1 isolates of subtype A and E. As shown in the examples, the use of both upstream primers can help equalize the efficiency of amplification of particular subtypes.

Amplification

Amplifications are carried out under conditions which enable amplification of all HIV-1 group M subtypes, but which are sufficiently stringent to avoid amplification of non-target sequences. Preferred amplification reaction conditions are described in the examples, in Mulder et al., 1994, *J. Clin. Microbiol.* 32(2):292–300, and in product insert of the AMPLICOR HIV-1 MONITOR Test. The exact conditions are not a critical aspect of the invention. Optimization of amplification conditions can be carried out routinely based on the guidance provided herein.

The primers and methods of the present invention may be used to detect either HIV-1 proviral DNA or HIV-1 RNA. The amplification of RNA using a reverse transcription/polymerase chain reaction (RT-PCR) is well known in the art and described in U.S. Pat. Nos. 5,322,770 and 5,310,652; Myers and Gelfand, 1991, *Biochemistry* 30(31):7661–7666; and Young et al., 1993, *J. Clin. Microbiol.* 31(4):882–886, each incorporated herein by reference. The RT-PCR amplification of HIV-1 RNA is described in Mulder et al, 1994, *J. Clin. Microbiol.* 32(2):292–300 and Holodniy et al, 1991, *J. Inf. Dis.* 163:802–865.

Sample preparation methods suitable for amplification of HIV-1 DNA and RNA are described in the literature. The particular method used is not a critical aspect of the present invention. One of skill in the art can select and optimize suitable sample preparation methods base on the guidance provided herein. Preferred sample preparation methods for use in the detection of HIV-1 proviral DNA are described in Casareale et al, 1992, *PCR Methods and Applications* 2:149–153 and Butcher and Spadoro, 1992, *Clin. Immunol. Newsletter* 12:73–76, both incorporated herein by reference. A preferred sample preparation kit for the detection of HIV-1 proviral DNA is commercially available as part of the Amplicor HIV-1. Test. Preferred sample preparation methods for use in the detection of HIV-1 RNA in plasma are described in Mulder et al, 1994, *J. Clin. Microbiol.* 32(2):292–300. A preferred sample preparation kit for the detection and/or quantitation of HIV-1 RNA is commercially available as part of the AMPLICOR HIV-1 MONITOR Test.

Analysis of Amplified Product

The amplification primers and methods of the present invention are suitable for any application which uses amplified nucleic acid. For example, cloning and/or sequencing of HIV-1 sequences is facilitated by the use of the present primers. Methods for detecting PCR amplified nucleic acids are well known in the art. The method used to analyze the amplified nucleic acid is not a critical aspect of the invention, and any suitable method may be used. Preferably, amplification of HIV-1 RNA is used as described in the examples to quantitate viral load.

Examples of methods for detecting amplified nucleic acid include analysis of amplification product by gel electrophoresis and detection by hybridization with complementary oligonucleotide probes. Suitable assay formats for detecting target-probe hybridization are well known in the art and include the dot-blot and reverse dot-blot assay formats.

In a dot-blot format, the amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe. Dot-blot detection of PCR amplification products is described in, for example, Saiki et al., 1986, *Nature* 324:163–166 and U.S. Pat. No. 5,468,613, both incorporated herein by reference.

In a reverse dot-blot format, the probes are immobilized on a solid support, such as a nylon membrane and the amplified target DNA is labeled. The target DNA is typically labeled during amplification by the incorporation of labeled primers. One or both of the primers can be labeled. The membrane-probe complex is incubated with the labeled amplified target DNA under suitable hybridization conditions, unhybridized target DNA is removed by washing under suitably stringent conditions, and the filter is then monitored for the presence of bound target DNA. Reverse dot-blot methods are described in, for example, Saiki et al., 1989, *Proc. Nad. Acad. Sci. USA* 86:6230 and U.S. Pat. No. 5,468,613, both incorporated herein by reference.

Alternatively, the reverse dot-blot assay can be carried out using a solid support having a plurality of probe hybridization sites or wells. For example, a microwell plate is particularly useful in large scale clinical applications of the present methods. Probes can be immobilized to a microwell plate either by passive binding or through a protein intermediate, such as bovine serum albumin (BSA), which adheres to microwell plates (see Tung et al., 1991, *Bioconjugate Chem.* 2:464–465, incorporated herein by reference). Reverse dot-blot methods carried out in a microwell plate are described in U.S. Pat. No. 5,232,829; Loeffelholz et al., 1992, *J. Clin. Microbiol.* 30(11):2847–2851; both incorporated herein by reference; Jackson et al., 1991, AIDS 5:1463–1467; Mulder et al, 1994, *J. Clin. Microbiol.* 32(2):292–300; the Amplicor HIV-1 Test product insert; and the AMPLICOR HIV-1 MONITOR Test product insert Preferably, detection and/or quantitation of the amplified product is carried out by hybridization with an oligonucleotide probe immobilized on a microwell plate using the reagents and protocols of the Amplicor HIV-1 Test or the AMPLICOR HIV-1 MONITOR Test. The use of the present methods to quantitate HIV-1 RNA is described further in the examples.

Alternatively, BSA-conjugated probes are bound to magnetic microparticles. The bound probes are hybridized in solution to labeled amplification product, and the resulting are removed from the solution magnetically. The magnetically immobilized hybridization duplexes are then detected as in the methods described above.

Another suitable assay method, referred to as a 5'-nuclease assay, is described in U.S. Pat. Nos. 5,210,015, and 5,487,972 and Holland et al., 1988, *Proc. Natl. Acad. Sci. USA* 88:7276–7280, each incorporated herein by reference. In the 5'-nuclease assay, labeled detection probes which have been modified so as to prevent the probes from acting as primers for DNA synthesis are added during the amplification reaction mixture. Any probe which hybridizes to target DNA during each synthesis step, i.e., during primer extension, is degraded by the 5' to 3' exonuclease activity of the DNA polymerase, e.g., Taq DNA polymerase. The degradation product from the probe is then detected. Thus, the presence of probe breakdown product indicates both that hybridization between probe and target DNA occurred and that the amplification reaction occurred. U.S. Pat. Nos. 5,491,063 and 5,571,673, both incorporated herein by reference, describe improved methods for detecting the degradation of probe which occurs concomitant with amplification.

The assay formats described above typically utilize labeled oligonucleotides to facilitate detection of the hybrid duplexes. Oligonucleotides can be labeled by incorporating a label detectable by spectroscopic, photochemical, biochemical, immunochemical, or chemical means. Useful labels include 32p, fluorescent dyes, electron-dense reagents, enzymes (as commonly used in ELISAS), biotin, or haptens and proteins for which antisera or monoclonal antibodies are available. Labeled oligonucleotides of the invention can be synthesized and labeled using the techniques described above for synthesizing oligonucleotides.

An alternative method for detecting the amplification of HIV-1 nucleic acid by monitoring the increase in the total amount of double-stranded DNA in the reaction mixture is described in Higuchi et al., 1992, *Bio/Technology* 10:413–417; Higuchi et al., 1993, *Bio/Technology* 11:1026–1030; and European Patent Publication No. 512, 334, each incorporated herein by reference. The detection of double-stranded target DNA relies on the increased fluorescence that ethidium bromide (EtBr) and other DNA binding labels exhibit when bound to double-stranded DNA. The DNA binding label is added to the amplification reaction mixture. Amplification of the target sequence results in an increase in the amount of double-stranded DNA, which results in a detectable increase in fluorescence.

The present invention also relates to kits, multicontainer units comprising useful components for practicing the present method. A useful kit contains primers for the PCR amplification of HIV-1 nucleic acid. A kit can also contain means for detecting amplified HIV-1 nucleic acid, such as oligonucleotide probes. In some cases, the probes are fixed to an appropriate support membrane. Other optional components of the kit include, for example, an agent to catalyze the synthesis of primer extension products, the substrate nucleoside triphosphates, means used to label (for example, an avidin-enzyme conjugate and enzyme substrate and chromogen if the label is biotin), the appropriate buffers for PCR or hybridization reactions, and instructions for carrying out the present method.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

Construction of a Quantitation Standard

Quantitation of viral load, as carried out using the AMPLICOR HIV-1 MONITOR Test, uses a Quantitation Standard (QS) which is amplified using the same primer pair, but which is detected using a separate probe. The QS is added to the test sample at a known concentration to provide a known reference signal. For a wide range of target concentrations, the signal generated from the amplified target or amplified QS is proportional to the amount present. The target copy number is calculated from a comparison of the signal generated from the amplification of the unknown target to the signal generated from the known QS.

The primers of the present invention amplify a region which is not fully encompassed within the QS included in the AMPLICOR HIV-1 MONITOR Test (the Amplicor QS). Thus, a new QS was constructed for use with the primers of the present invention. The new QS was constructed from the Amplicor QS by extending the Amplicor QS sequence to encompass the binding sites of SKCC1 (SEQ ID NO: 3) and SKCC3 (SEQ ID NO: 4). The resulting QS is detectable using the QS-specific probe used in the AMPLICOR HIV-1 MONITOR Test The construction of a plasmid containing the new QS sequence, from which the QS RNA is transcribed, can be carried out using standard techniques as described below.

The Amplicor QS, obtained from the AMPLICOR HIV-1 MONITOR Test, is amplified using SK145 (SEQ ID NO: 1) and SK151 (SEQ ID NO: 7) under conditions essentially as described in example 2, below. The amplification yields a DNA product which contains primer binding sites for SK145 (SEQ ID NO: 1) and SK151 (SEQ ID NO: 7) and retains the internal sequence which contains the binding site of the QS-specific probe.

Next, the resulting amplified product is extended to encompass the primer binding site of SKCC1 (SEQ ID NO: 3) and a linker is added to enable cloning of the product. This is achieved by reamplifying the product using SK145 (SEQ ID NO: 1) extended at the 5' end to include a HindIII linker and SKCC1 (SEQ ID NO: 3). Suitable amplification conditions are described in Kellogg and Kwok, 1990, in PCR Protocols: A Guide to Methods and Applications, (ed. Innis et al.), Academic Press, San Diego, Calif.):337–347, with the exception that a lower annealing/extension temperature (e.g., 42° C) is used to allow hybridization of SKCC1 (SEQ ID NO: 3).

Next, the resulting amplified product is further extended to encompass the primer binding site of SKCC3 (SEQ ID NO: 4) and a second linker is added at the other end to enable cloning of the product. This is achieved by amplifying the product using SK145 (SEQ ID NO: 1) extended at the 5' end to include a HindIII linker, as described above, together with SKCC3 (SEQ ID NO: 4) extended at the 5' end to include an XBa I linker, using the same amplification conditions as above.

Next, the amplified product is inserted into a plasmid. The amplified DNA and plasmid pSP64 (Promega, Madison, Wis.) are separately digested with HindIII and XBa I, and then ligated using standard procedures. Competent cells are transformed with recombinant plasmids and a clone is obtained which contains the correct insert. The cloned insert in the resulting recombinant plasmid should be sequenced to determine that no mutations are introduced into the primer or probe binding sites.

The QS RNA is transcribed from the recombinant plasmid that contains the QS sequence using a MEGAscript™ SP6 kit (Ambion, Inc., Austin, Tex.).

EXAMPLE 2

HIV-1 RNA Quantitation

This examples describes an assessment of the relative efficiency of amplifications from various HIV-1 isolates. For comparison, amplifications also were carried out using the AMPLICOR HIV-1 MONITOR Test Kit.

The HIV-1 isolates were obtained from HIV-1 positive clinical samples. A region of the gag gene was cloned and sequenced using standard techniques, and the subtype of the cloned HIV-1 was determined based on the sequence. A number of these HIV-1 isolates were discovered to be novel. For this example, particular isolates were chosen which, based on the nucleotide sequences, were expected to be problematical for the AMPLICOR HIV-1 MONITOR Test. In addition, isolates were used which were representative of the sequence variation present in the group M subtypes.

Target Nucleic Acid

Plasmids containing a region of the HIV-1 gag gene from each isolate were constructed and HIV-1 RNA templates were transcribed essentially as described in Holodniy et al, 1991, *J. Inf. Dis.* 163:802–865. Stock solutions of each template were made up and the template concentrations were assayed. The stock solutions were diluted based on the estimated relative concentrations such that the concentration of template added to each reaction was the same. The absolute number of copies of template added to the reactions was approximately 4000–8000.

Quantitation Standard

A QS as described in example 1 was introduced into each reaction mixture at a known concentration, typically approximately 100 copies per reaction.

Primers

Reactions A–F were carried out using the following primer combinations.

| Primer Combinations Compared | |
|---|---|
| Reaction | Primer Combination |
| A | SK462 (SEQ ID NO: 5): SK431 (SEQ ID NO: 6) |
| B | SM45 (SEQ ID NO: 1) SK151 (SEQ ID NO: 7) |
| C | SK145 (SEQ ID NO: 1) SKCC1 (SEQ ID NO. 3) |
| D | SK145 (SEQ ID NO: 1): and 5K145M2 (SEQ ID NO: 2) SKCC1 (SEQ ID NO: 3) |
| E | SK145 (SEQ ID NO: 1) SKCC3 (SEQ ID NO: 4) |
| F | SK145 (SEQ ID NO: 1) and SK145M2 (SEQ ID NO: 2) SKCC3 (SEQ ID NO: 4) |

All primers were biotinylated at the 5' end to enable detection in a reverse dot-blot, microwell plate format. Sequences of the additional primers not described above are provided below, shown in a 5' to 3' orientation.

| | Upstream Primer |
|---|---|
| SK462 (SEQ ID NO: 5) | AGTTGGAGGACATCAAGCAGCCATGCAAAT |
| | Downstream Primers |
| SK431 (SEQ ID NO: 6) | TGCTATGTCAGTTCCCCTTGGTTCTCT |
| SK151 (SEQ ID NO: 7) | TGCTATGTCACTTCCCGFFGGTTCTCT |

Amplification

Amplification reaction A was carried out using the reagents and conditions of the AMPLICOR HIV-1 MONITOR Test.

Amplification reaction B was carried out in 100 1 volumes containing the following reagents:

HIV-1 template RNA
QS RNA
50 $\mu$M Bicine, pH 8.3
111 $\mu$M K(OAc)
3.6 $\mu$M Mn(OAc)$_2$
500 $\mu$M dUTP
300 $\mu$M each dATP, dCTP, and dGTP
50 $\mu$M dTTP
15% glycerol
0.2 $\mu$M each biotinylated primer
2 units of UNG*

10 units of rTth DNA polymerase*

*manufactured and developed by Hoffmann-La Roche and marketed by Perkin Elmer (Norwalk, Conn.).

Amplification reactions C and D were carried out under conditions essentially as used in reaction B, but with the following changes:

100 mM K(OAc)
500 $\mu$M each dATP, dCTP, and dGTP
7.5% Glycerol
10 units of UNG Amplification reactions E and F were carried out under conditions essentially as used in reactions C and D, but with the exception that a 10% glycerol concentration was used. The minor differences in reaction mixtures resulted from prior optimization of the amplification conditions for each primer pair.

Amplification reactions B–F were carried out in a TC9600 DNA thermal cycler (Perkin Elmer, Norwalk, Conn.) using the following temperature profile:

Pre-reaction incubation: 50° C. for 2 minutes
Reverse-transcription 60° C. for 30 minutes;
4 cycles: denature: 95° C. for 10 seconds,
    anneal: 55° C. for 10 seconds, and
    extend: 72° C. for 10 seconds;
26 cycles: denature: 90° C. for 10 seconds,
    anneal: 60° C. for 10 seconds, and
    extend: 72° C. for 10 seconds;
Final extension: 72° C. for 15 minutes;

Detection of Amplified Product by Probe Hybridization

Amplified products were detected using the reagents and protocols of the AMPLICOR HIV-1 MONITOR Test. The estimated initial target concentration was calculated as described therein.

Results

In the AMPLICOR HIV-1 MONITOR Test quantitation method, the initial target concentration is estimated from a comparison of the signal generated after amplification of the target to the signal generated after amplification of a known concentration of QS. Because the known concentration of the QS is the pre-amplification value, whereas the signals compared are post-amplification signals, changes in the relative efficiency of amplification will affect the estimate of the initial concentration of the unknown target. The AMPLICOR HIV-1 MONITOR Test quantitation is calibrated based on the amplification efficiency of HIV-1 subtype B. It is known that other HIV-1 subtypes may be amplified with lower efficiency and, consequently, that the estimated target concentration would be an under-estimate of the true concentration.

In the present experiment, target RNA was added to each reaction at a known concentration. Thus, the relative amplification efficiency for each isolate can be determined by comparing the estimated target concentrations. Because the AMPLICOR HIV-1 MONITOR Test quantitation is calibrated based on the amplification efficiency of HIV-1 subtype B, the estimated target concentration of subtype B (clone 105-1) was used as a reference. For each isolate, the estimated target concentration for subtype B (clone 105-1) was divided by the estimated target concentration for the isolate to provide a measure of the relative amplification efficiency. These relative amplification efficiencies are reported in the table below. An entry of "- - -" indicates that the reaction was not carried out.

Efficiency Relative to Subtype B

| Clone | Subtype | A | B | C | D | E | F |
|---|---|---|---|---|---|---|---|
| 113-1 | A | 694.3 | 1.7 | 0.9 | 1.4 | 1.4 | 0.9 |
| 113-2 | A | 19 | — | 1.3 | 1.1 | 1.3 | 0.6 |
| 114-1 | A | 12.4 | — | 1.4 | 1.3 | 0.7 | 0.9 |
| 114-2 | A | 9.8 | 1.2 | 1.1 | 1.8 | 1.5 | 0.8 |
| 115-1 | A | 497.6 |  | 0.8 | 1.2 | 1 | 1.6 |
| 115-2 | A | 646.4 | 2.4 | 1 | 1.5 | 0.9 | 1.4 |
| 105-1 | B | 1 | 1 | 1 | 1 | 1 | 1 |
| 101-15 | C | 7.3 | — | 1.1 | 3.5 | 1.9 | 1.4 |
| 107-6 | D | 0.8 | — | 0.6 | 0.7 | 0.7 | 0.8 |
| 308-1 | D | 0.9 | — | 0.6 | 0.7 | 0.7 | 0.5 |
| 110-5 | E | 520.7 | 465.7 | 3.5 | 1.2 | 4.6 | 0.8 |
| 111-6 | E | 0.8 | — | 1.1 | 1.6 | 0.9 | 1.1 |
| 112-7 | E | 3.3 | 0.8 | 1.5 | 1.9 | 1.2 | 1.4 |
| 106-1 | G | 1.9 | — | 2.3 | 2 | 1.8 | 1.5 |
| 108-3 | G | 0.6 | — | 0.5 | 0.8 | 0.5 | 0.5 |
| 109-1 | G | 32.5 | 1 | 0.5 | 0.6 | 0.6 | 0.3 |

The results demonstrate that the AMPLICOR HIV-1 MONITOR Test (reaction A) amplified the different HIV-1 isolates with a significant variation in the efficiency. Several of the isolates, including the subtype E isolate, clone 110-5, were amplified with an efficiency at least about 500-fold lower than the efficiency of amplification of subtype B, clone 105-1.

Although not all of the isolates were tested, use of the primer pair SK145 (SEQ ID NO: 1) and SK151 (SEQ ID NO: 7) (reaction B) appeared to improve the uniformity of amplification efficiency significantly. However, the subtype E isolate, clone 110-5, still was amplified with an efficiency about 500-fold lower than the efficiency of amplification of subtype B, clone 105-1.

The use of SK145 (SEQ ID NO: 1) and SKCC1 (SEQ ID NO: 3) (reaction C) enabled amplification of all the isolates, including the subtype E isolate, clone 110-5, with an efficiency within about 3-fold of the efficiency of amplification of subtype B, clone 105-1. The addition of SK145M2 (SEQ ID NO: 2) (reaction D) further improved the efficiency of amplification of isolate 110–5 to be essentially equivalent to that of the subtype B reference strain.

Similarly, the use of SK145 (SEQ ID NO: 1) and SKCC3 (SEQ ID NO: 4) (reaction E) enabled amplification of all the isolates, including the subtype E isolate, clone 110-5, with an efficiency within about 5-fold of the efficiency of amplification of subtype B, clone 105-1. The addition of SK145M2 (SEQ ID NO: 2) (reaction F) further improved the efficiency of amplification of isolate 110-5 to be essentially equivalent to that of the subtype B reference strain.

EXAMPLE 3

Quantitation of HIV-1 in Clinical Samples

In this example, 30 clinical samples obtained from seropositive patients from Senegal were assayed for the presence of HIV-1 RNA. The subtypes present in the clinical samples were not determined. However, as subtypes A and D are common in this region of Africa, it was expected that some of the clinical samples either would not be amplified or would not be amplified efficiently using the AMPLICOR HIV-1 MONITOR Test.

Samples were prepared as follows. Plasma specimens (80–250 $\mu$l) were combined with 20 $\mu$l of 0.25% (w/v) red Estapor polystyrene microspheres (Bangs Laboratories, Inc., Carmel, Ind.) in a 1.5 ml conical centrifuge tube and centrifuged for 1 hour at 25,300 X g at 4° C. The supernatant was aspirated off and the pellet was resuspended in 250 $\mu$l lysis buffer (50 $\mu$l of lysis buffer equals 6.7 $\mu$l of 30 U/$\mu$l RNasin (Promega, Madison, Wis.); 0.67 $\mu$l of 100 mM DTF; 2 $\mu$l of 10% NP40 (Pierce, Rockford, Ill.); 0.25 $\mu$l of 4 mg/ml poly-rA RNA; and 40.4 $\mu$l of Depc-treated $H_2O$). The pellets were incubated at room temperature for at least 15 minutes and vortexed to ensure mixing.

Amplifications were carried out in 100 $\mu$l reactions containing 50 $\mu$l of the viral lysate solution and 50 $\mu$l of a 2X mixture of amplification reagents formulated such that the final reagent concentration was as described above. Approximately 100 copies of the appropriate QS were added to each reaction as part of the reagent mixture. Detection of the amplified product was carried out using the reagents and protocols of the AMPLICOR HIV-1 MONITOR Test, as described above.

Amplifications of each sample were carried out using the following primers combinations.

Primer Combinations Compared

| Reaction | Primer Combination |
|---|---|
| A | SK462 (SEQ ID NO: 5) |
|  | SK431 (SEQ ID NO: 6) |
| B | SK145 (SEQ ID NO: 1) |
|  | SKCC1 (SEQ ID NO: 3) |
| C | SK145 (SEQ ID NO: 1) and SK145M2 (SEQ ID NO: 2) |
|  | SKCC1 (SEQ ID NO: 3) |

The results, expressed in copies of HIV-1 template per ml of plasma, are summarized below.

Estimated Target Concentration (copies/ml)

| Isolate | A | B Duplicate | | C Duplicate | |
|---|---|---|---|---|---|
| DKN 035 | 0 | 800 | 1860 | 1600 | 1100 |
| DKN 079 | 360 | 30060 | 37240 | 91780 | 152300 |
| DKN 154 | 1140 | 21660 | 54560 | 68820 | 67120 |
| DKN 162 | 0 | 16020 | 25980 | 64340 | 21880 |
| DKN 162 | 0 | 12180 | 10520 | 14300 | 18320 |
| DKN 169 | 0 | 3140 | 7000 | 5651 | 8047 |
| DKN 171 | 1180 | 640 | 500 | 560 | 1040 |
| DKN 282 | 560 | 3400 | 4360 | 5560 | 3460 |
| DKN 402 | 340 | 4260 | 10520 | 7000 | 5060 |
| MBN 26 | 27740 | 16940 | 19220 | 16700 | 18680 |
| MBN 31 | 180 | 1820 | 1820 | 1720 | 2240 |
| MBN 34 | 840 | 2160 | 2200 | 3100 | 3120 |
| MIH 002 | 2320 | 51320 | 121100 | 144180 | 123900 |
| MIH 012 | 2960 | 33620 | 40920 | 40740 | 75840 |
| MIH 013 | 30360 | 31980 | 55360 | 42800 | 71220 |
| MIH 030 | 17625 | 178500 | 273938 | 169750 | 189625 |
| MIH 053 | + | 534960 | 231620 | 530900 | 878340 |
| MIH 055 | 10560 | 43960 | 54220 | 49400 | 37400 |
| MIH 074 | 5700 | 3980 | 6020 | 3640 | 4940 |
| MIH 112 | 30480 | 271980 | 490780 | 423600 | 416140 |
| MIH 157 | 520 | 165480 | 82920 | 169980 | 146320 |
| MIN 003a | 1300 | 57720 | 21620 | 35380 | 34560 |
| MIN 003b | 1760 | 32820 | 30940 | 27760 | 26600 |
| MIN 017 | 540 | 437380 | 375120 | 447740 | 902780 |
| MIN 067 | 0 | 0 | 0 | 0 | 0 |
| MIN 126 | 44320 | 63600 | 38460 | 56680 | 40300 |
| MIN 139 | 460 | 146320 | 142800 | 94520 | 105600 |
| MIN 146 | 200 | 49920 | 32100 | 19900 | 30400 |
| MIN 217 | 0 | 3220 | 1880 | 2320 | 2580 |
| MIN 589 | 154780 | 267740 | 127100 | 144160 | 228040 |

The results indicate that the primers of the present invention, combinations B and C, enabled amplification from more of the clinical samples. The primer combinations B and C enabled amplification from all but 1 of the 30 samples. In contrast, the AMPLICOR HIV-1 MONITOR Test failed to amplify 6 out of 29 samples. The amplification of sample MIH 053 using the AMPLICOR HIV-1 MONITOR Test resulted in a strong target signal, but failed to generate a QS signal. Thus, the sample was not quantitatable and is marked as "+" in the above table.

In addition, for a significant number of the samples, the copy number estimated using either primer combination B or C was significantly higher than that estimated using the AMPLICOR HIV-1 MONITOR Test. Based on the amplification efficiency variability demonstrated in example 2, above, the lower estimates of template concentration obtained using the AMPLICOR HIV-1 MONITOR probably resulted from significantly lower amplification efficiencies.

Viral RNA was not detected in sample MIN 067. However, it is not known if this is due to unseen variability in the target sequence which interfered with either primer hybridization or probe hybridization, or some other cause.

We claim:

1. An oligonucleotide primer for the amplification of human immunodeficiency virus type 1 (HIV-1) nucleic acid, wherein said oligonucleotide primer is selected from the group consisting of SKCC1 (SEQ ID NO: 3) and SKCC3 (SEQ ID NO: 4).

2. A pair of oligonucleotide primers consisting of SK145 (SEQ ID NO: 1) and SKCC1 (SEQ ID NO: 3).

3. A set of oligonucleotide primers consisting of a pair of oligonucleotide primers of claim 2 and SK145M2 (SEQ ID NO: 2).

4. A pair of oligonucleotide primers consisting of SK145 (SEQ ID NO: 1) and SKCC3 (SEQ ID NO: 4).

5. A set of oligonucleotide primers consisting of a pair of oligonucleotide primers of claim 4 and SK145M2 (SEQ ID NO: 2).

6. A kit for detecting human immunodeficiency virus type 1 (HIV-1) nucleic acid, wherein said kit comprises an oligonucleotide primer of claim 1.

7. A kit for detecting human immunodeficiency virus type 1 (HIV-1) nucleic acid, wherein said kit comprises a pair of oligonucleotide primers of claim 2.

8. A kit for detecting human immunodeficiency virus type 1 (HIV-1) nucleic acid, wherein said kit comprises a set of oligonucleotide primers of claim 3.

9. A kit for detecting human immunodeficiency virus type 1 (HIV-1) nucleic acid, wherein said kit comprises a pair of oligonucleotide primers of claim 4.

10. A kit for detecting human immunodeficiency virus type 1 (HIV-1) nucleic acid, wherein said kit comprises a set of oligonucleotide primers of claim 5.

11. A method for amplifying human immunodeficiency virus type 1 (HIV-1) nucleic acid, wherein said method comprises carrying out a polymerase chain reaction using SKCC1 (SEQ ID NO: 3) or SKCC3 (SEQ ID NO: 4).

12. A method of claim 11, wherein said polymerase chain reaction is carried out using SK145 (SEQ ID NO: 1) and SKCC1 (SEQ ID NO: 3).

13. A method of claim 12, wherein said polymerase chain reaction is carried out using SK145M2 (SEQ ID NO: 2).

14. A method of claim 11, wherein said polymerase chain reaction is carried out using SK145 (SEQ ID NO: 1) and SKCC3 (SEQ ID NO: 4).

15. A method of claim 11, wherein said polymerase chain reaction is carried out also using SK145M2 (SEQ ID NO: 2).

\* \* \* \* \*